United States Patent [19]

Kluger et al.

[11] 4,211,725
[45] Jul. 8, 1980

[54] NITROGEN CONTAINING COMPOSITIONS

[75] Inventors: Edward W. Kluger, Pauline; Tien-Kuei Su; Teresa J. Thompson, both of Spartanburg, all of S.C.

[73] Assignee: Milliken Research Corporation, Spartanburg, S.C.

[21] Appl. No.: 967,391

[22] Filed: Dec. 7, 1978

Related U.S. Application Data

[62] Division of Ser. No. 850,456, Nov. 10, 1977.

[51] Int. Cl.$^2$ .............................................. C07C 87/14
[52] U.S. Cl. .......................... 260/583 P; 260/465.5 R
[58] Field of Search ..................................... 260/583 P

[56] References Cited

U.S. PATENT DOCUMENTS 3,119,872  1/1964  Scott ................................. 260/583 P
3,151,160  9/1964  Spivack ......................... 260/583 P X Primary Examiner—John Doll
Attorney, Agent, or Firm—H. William Petry; Terry T. Moyer

[57] ABSTRACT

Novel nitrogen containing compounds are provided which are represented structurally as

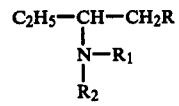

wherein R is CN or $CH_2NH_2$, and $R_1$ and $R_2$ are hydrogen or $C_2H_5$—CH—$CH_2R$ wherein R is as previously defined.

2 Claims, No Drawings

NITROGEN CONTAINING COMPOSITIONS

This is a divisional of application Ser. No. 850,456, filed Nov. 10, 1977.

This invention relates to novel chemical compositions. In one aspect it relates to novel nitrogen containing compositions. In another aspect it relates to novel amine compositions. In yet another aspect, the invention relates to di- and polyamine epoxy curing agents.

Chemical compositions, particularly novel chemical compositions, are constantly being sought by the chemical industry. Such chemical compositions are generally sought to improve properties of existing chemical compositions, or as intermediates, to provide chemical compositions having improved physical, chemical and/or toxicological properties. Heretofore, aromatic compositions have been employed in the production of numerous products, such as polyurethane foams, polyamides, and curing agents for resinifying polyepoxides. However, recently, such aromatic structures or compounds containing same have become suspect as possessing toxicological properties which are believed hazardous to those working with or employing such compounds. Therefore, new and improved chemical compositions, including intermediate products or adducts, are constantly being sought which can be economically produced and do not possess suspect toxicological and other undesirable properties. Further, with the wide use of polyepoxides, and the need of curing or resinifying agents for such polyepoxide, new and improved epoxy curing agents are being sought which do not possess obnoxious odors, cause irritation to the skin of the operator, or possess other hazardous and/or toxicological properties. However, in obtaining new curing or resinifying agents for polyepoxides, the resulting products must have sufficient hardness and strength, often at elevated temperatures. Further, it is extremely desirable that the cured polyepoxide compositions have substantial resistance to water and/or solids.

It is therefore an object of the present invention to provide novel chemical compositions. Another aspect of the invention is to provide novel nitrogen containing compositions which do not contain aromatic moieties therein and which do not create toxicological problems for the processor or user of such compounds. Further, it is an object of the invention to provide new and improved curing and resinifying agents for polyepoxides which do not contain obnoxious odors, toxicological properties and which do not sacrifice the desired hardness and strength of cured products. These and other objects, advantages and features of the invention will be apparent to those skilled in the art from a reading of the following detailed description.

According to the present invention, we have now discovered novel, non-aromatic, nitrogen containing compounds which can be employed as epoxy curing agents, as intermediates for the preparation of epoxy curing agents and fuel oil additives, as intermediates for the production of polyurethane foams, polyamides, and β-amino acids, which are economical to manufacture, do not possess undesired toxicological properties, and which, in most instances, are equivalent or superior to the prior art compositions employed in such uses. Broadly, the present invention resides in novel, non-aromatic nitrogen containing compounds represented structurally as

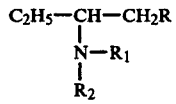

wherein R is CN or $CH_2NH_2$, and $R_1$ and $R_2$ are hydrogen or $C_2H_5$—CH—$CH_2R$ wherein R is as previously defined.

The nitrogen containing compounds under the present invention are each derived from 2-pentenenitrile. Initially, an effective amount of a nucleophilic agent is reacted with the 2-pentenenitrile so that the 2-pentenenitrile undergoes an addition reaction with the nucleophilic agent to form a reaction mixture containing a monocyanoamine, a dicyanoamine, and a mixture of dimers. The amount of nucleophilic agent employed in the addition reaction with the 2-pentenenitrile can vary widely but will generally be in a molar ratio with the 2-pentenenitrile of from about 1:1 to about 20:1.

The term "nucleophilic agent" as used herein is to be understood to be any compound capable of being reacted with the 2-pentenenitrile in an addition reaction activated by heat and/or a catalyst. Examples of suitable nucleophilic agents are aqueous ammonia, ammonium hydroxide, anhydrous ammonium, ethylenediamine, propylenediamine, and the like, and low molecular aliphatic alcohols, such as those alcohols containing from 1 to about 10 carbon atoms. Typical of such aliphatic alcohols are methanol, ethanol, isopropanol, butanol, hexanol, hepthanol, and decanol.

The particular nucleophilic agent employed in the addition reaction with the 2-pentenenitrile will, of course, have some effect upon the overall composition of the reaction mixture.

Any suitable metal addition catalyst can be employed to carry out the addition reaction. For instance, the catalyst can be Raney nickel, ruthenium, cobalt, iron, palladium, platinum, osmium, iridium, copper, and rhodium. As is evident, such catalyst can be either in the free metal state or can be extended on a support, such as charcoal, aluminum, kieselguhr and the like.

The temperature at which the addition reaction is carried out can vary. However, generally it is desirable to conduct such a reaction at a temperature in the range of from about 50° C. to about 180° C. for a period of time effective to allow the addition reaction to go to substantial completion. Generally, such can be accomplished in a period of time of from about 1 to about 10 hours. To further illustrate such, the following reaction of 2-pentenenitrile with concentrated aqueous ammonia, ammonium hydroxide, and anhydrous ammonium is set forth as equations 1, 2, and 3, respectively, hereinafter.

REACTION 1

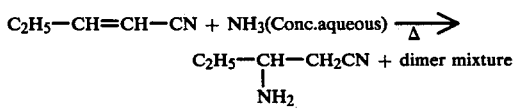

REACTION 2

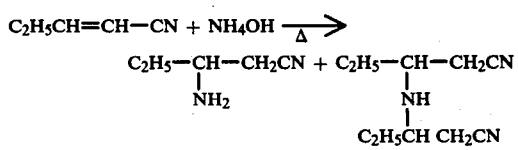

REACTION 3 -continued

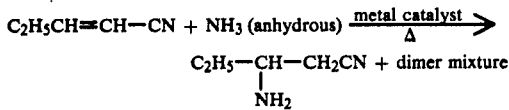

The dimer mixture formed by the reaction of the 2-pentenenitrile with concentrated aqueous ammonia is believed to be a mixture of isomers having the general structures

ISOMER CONFIGURATION 1

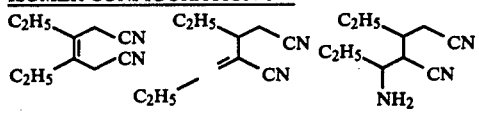

Whereas the dimer formed as a result of the reaction between anhydrous ammonia and the 2-pentenenitrile is believed to be

ISOMER CONFIGURATION 2

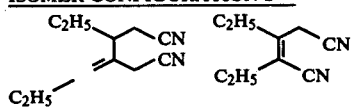

The products contained in the reaction mixture resulting from the addition of a nucleophilic agent to the 2-pentenenitrile can readily be separated one from another by any suitable means, such as by distillation under vacuum. Once the products have been separated and the desired constituents obtained, such constituents can then be subjected to additional reactions such as a reduction reaction to produce the corresponding polyamine. To illustrate such, the following reactions are set forth. In the reactions, the 3-aminopentenenitrile obtained in the above Reactions 1–3 is reduced with hydrogen in the presence of ammonia, both in the presence and absence of a solvent, such as methyl alcohol, to produce the corresponding diamine, namely 1,3-diaminopentane in high yield.

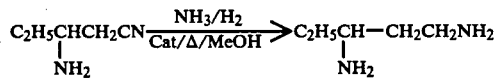

The temperature at which the above described reduction of the 3-aminopentanenitrile is carried out can vary widely. However, generally the temperature will be within a range of from about 80° to 150° C. Likewise, the period of time required for the reaction to go to substantial completion can vary widely, such being dependent on the particular catalyst employed, as well as the temperature at which such reaction is carried out. Generally, however, the reaction proceeds to completion when the reactants are contacted at the required temperature for a period of time of from about 0.5 to about 4 hours.

In carrying out the reduction of the 3-aminopentanenitrile any suitable reduction catalyst can be employed. Typical of such reduction catalyst are Raney nickel, iron, palladium, platinum, ruthenium, cobalt, rhodium, osmium, iridium, including salts and oxides thereof, and the like. Further, such catalysts can be in their free metal state or extended on a support such as charcoal, aluminum, kieselguhr and the like.

The 1,3-diaminopentane produced from the reduction of the 3-aminopentanenitrile can, if it is desired, be cyanoethylated with acrylonitrile in the presence of an acid catalyst. Similarly, if one desires, the 3-aminopentanenitrile, rather than being reduced, can likewise be subjected to cyanoethylation with acrylonitrile in the presence of a catalyst to form the dicyanolethylated product N-(2-cyanoethyl)-3-aminopentanenitrile.

REACTION 5

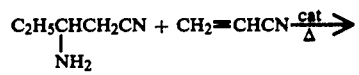

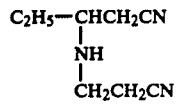

In conducting such a cyanoethylation reaction with acrylonitrile any suitable acid catalyst can be employed. Typical of such catalysts are p-toluene sulfonic acid and acetic acid salts. The temperature at which the cyanoethylation can be conducted can vary widely but generally such a reaction will be carried out at a temperature of from about 50° C. to about 120° C. for a period of time of from about 0.5 to about 5 hours. Of course, as is evident, the only criteria is that reaction conditions be employed which will allow the cyanoethylation to go to the desired degree of completion without the formation of undesirable side products.

To further illustrate the cyanoethylation of 1,3-diaminopentane the following equations are set forth. It should be noted that when 1,3-diaminopentane is reacted with one mole of acrylonitrile, the mono-cyanoethylated products N-(2-cyanoethyl)1,3-diaminopentanes, will be formed; whereas, when two moles of acrylonitrile are employed in the cyanoethylation of 1,3-diaminopentane the dicyanolethylated product, N,N'-di-(2-cyanoethyl)-1,3-diaminopentane, will be formed.

REACTION 6

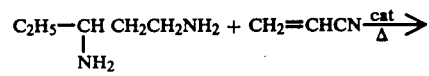

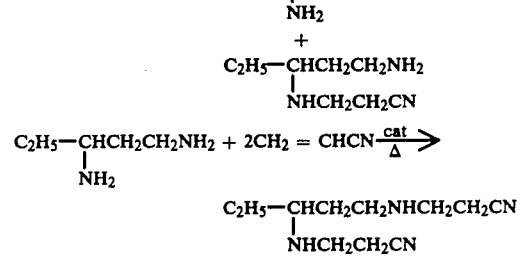

In addition to the above reactions, one skilled in the art can readily depict numerous other reactions which can be carried out to produce desired chemical compositions from the 3-aminopentanenitrile or 1,3-diaminopentane. Thus, such compounds clearly illustrate new and useful intermediates for the production of desired chemical compounds.

As previously stated, when 2-pentenenitrile is reacted with concentrated aqueous ammonia, a monocyanoamine, 3-aminopentanenitrile, and a mixture of dimers, 3,4-diethyl-3-hexenedinitrile and 1,3-dicyano-2-ethyl-3-hexene, are formed. Also, as previously stated, the dimer mixture can readily be separated, from the monocyanoamine, by any suitable means, such as vacuum distillation. In addition, when the 2-pentenenitrile is reacted with anhydrous ammonia in the presence of a metal catalyst, the monocyanoamine, 3-aminopentanenitrile, and a dimer mixture, 3,4-diethyl-3-hexenedinitrile, and 1,3-dicyano-2-ethyl-3-hexene are formed. The dimer mixture as previously stated, can readily be separated from the monocyanoamine, 3-aminopentanenitrile, by any suitable means such as vacuum distillation.

The dimer mixture which has been separated from the monocyanoamine can be reduced with a hydrogen in the presence of an amine, such as ammonia, ammonia hydroxide, and the like, and a suitable solvent, such as a low molecular weight alcohol containing from about 1 to 10 carbon atoms, as previously defined, to provide a mixture of cyclized products and diamines. The formation of the cyclized products and diamines from the before mentioned dimer mixture are illustrated by the following reaction.

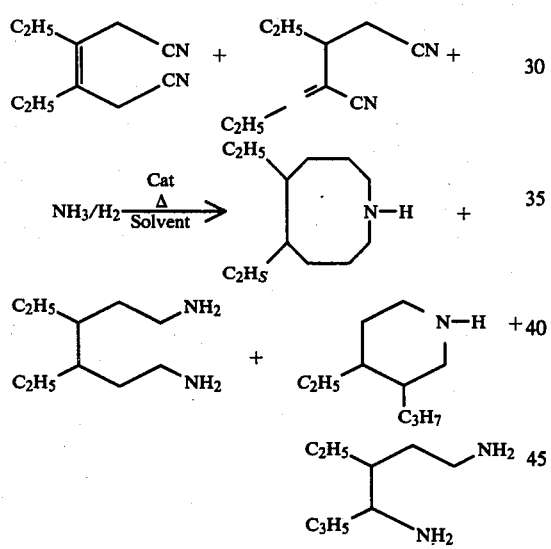

The cyclized products illustrated above can then be separated from the diamine constituents by any suitable means, such as vacuum distillation.

Any suitable reduction catalyst can be employed in the reduction of the dimer constituents to provide the mixture of cyclized products indicated above. Illustrative of such catalyst are Raney nickel, iron, palladium, platinum, cobalt, ruthenium, rhodium, osmium, iridium, and the like. Further, such catalysts can be either a free metal type catalyst or can be extended on a suitable support such as silicone, charcoal, aluminum, kieselguhr and the like.

The conditions at which the reduction of the dimers are carried out to provide the mixture of cyclized products can vary widely. Generally, however, such reduction is carried out at a temperature of from about 80° C. to about 150° C. for a period of time effective to allow the desired cyclization of the dimers to go to substantial completion. While the time may vary for such cyclization of the dimers, such being due in part to the particular catalyst employed, its activity, as well as the conditions at which the reduction reaction is carried out, generally such will be from about 0.5 to about 4 hours.

If desired, the cyclized products can thereafter be subjected to separation techniques, such as vacuum distillation, to recover a desired constituent which can thereafter be employed to carry out numerous other reactions to provide desired product. Thus, the above procedure clearly indicates the formation of novel cyclized products which can be subsequently reacted and thus have valuable uses as desired intermediate compositions.

One particular important use for the novel compounds of the subject invention, especially the polyamine constituents, is their use as epoxy curing agents for polyepoxides. The polyepoxides which can be cured at elevated temperatures using the polyamine compounds as herein described are those polyepoxides possessing at least two.

groups. These groups may be terminal, i.e.,

groups or they may be in an internal position. However, especially desirable results can be obtained when the epoxy groups are terminal. The polyepoxides may be saturated or unsaturated, aliphatic, cycloaliphatic, aromatic or heterocyclic, and may be substituted such as with hydroxyl groups, ether radicals and the like. Further, the polyepoxides can be monomeric or polymeric. Such polyepoxides, and their preparation, are well known in the art.

The curing of the polyepoxides with the above-described polyamine curing agents of the present invention may be accomplished by mixing the two components together. While the reaction between the two components occurs slowly at room temperature, improved results can be obtained if the mixture is heated to a temperature of from about 50° C. to about 280° C. for a period of time of from about 1 to about 12 hours and thereafter post curing the reaction product for an additional period of time of from about 1 to about 8 hours at a temperature of from about 140° C. to about 225° C. With small casting curing of the reaction, mixture can be obtained by heating the reaction mixture for about two hours at a temperature of from about 80° to 100° C. and thereafter post curing the reaction product at a temperature of from about 140° C. to 225° C. for an additional two hours or so.

The amount of the polyamine substituted cycloaliphatic compound employed as the curing agent in the cure of the polyepoxide may vary widely. However, the amount of such curing agent will generally range from about 5 parts per 100 parts of polyepoxide up to about 50 parts per 100 parts of polyepoxide. Especially desirable results are obtained when the curing agent is employed in amounts varying from about 10 to about 30 parts per 100 parts of polyepoxide.

In curing polyepoxides, it is generally desirable that the polyepoxide be in a mobile condition when the curing agent is added to insure uniform mixing. If the polyepoxide is extremely viscous or solid at room or casting temperature, the polyepoxide may be heated to reduce the viscosity or a volatile liquid solvent which can escape from the polyepoxide composition containing the polyamine cycloaliphatic curing agents by evaporation before and/or during the curing of such polyepoxide-polyamine cycloaliphatic composition can be added to the polyepoxide to reduce its viscosity. Typical of such volatile liquid solvents are ketones, such as acetone, methyl ethyl ketone and the like, ethers, such as ethyl acetate, butyl acetate and the like, ether alcohols, such as methyl, ethyl or butyl ethers of ethylene glycol and chlorinated hydrocarbons, such as chloroform.

In addition to the use of the polyamines of the subject invention as epoxy curing agents, many other uses can readily be envisioned by those skilled in the art. As previously stated, not only do the compositions of the subject invention find utility as epoxy curing agents but such composition, especially the dye and polyamine constituents can be employed as oil and fuel aductive intermediates, the cyanoamines can be hydrolyzed into $\beta$-amino acids. Further, the polyamines may be employed for the formation of diisocyanate compositions for the incorporation into polyurethane compositions, and the compound may be further reacted to form new and novel and useful polyamides.

In order to more fully describe the preparation and use of the novel compounds of the present invention the following examples are given. However, such examples are presented for illustration only and are not to be construed as unduly limiting the scope of the present invention. Unless otherwise indicated, all parts and/or percentages given in the examples are by weight.

EXAMPLE 1

In a 1000 cc rocking autoclave was placed 68.9 gm (0.85 mole) of 2-pentenenitrile, and 20 gm of Raney nickel. The autoclave was sealed and 300 gm of liquid ammonia was added. The autoclave was then heated at 210° F. for 4½ hours. On cooling, the reaction mixture was filtered from the nickel. The crude product was then distilled under vacuum to give 19.4% cyanoamine, 38.0% dimer, and 42.7% starting material. The IR, NMR, and GC mass spectra of the component boiling at 90° C. (15 mmHg) was consistent with the cyanoamine, 3-aminopentenenitrile. The elemental analysis was also in agreement with this structure:

Calc. for $C_5H_{10}N$: C, 61.22%; H, 10.20%; N, 28.57%. Found: C, 60.63%; H, 10.18%; N, 27.98%.

The IR, NMR, and GC mass spectra of the component boiling at 98° C. (1 mmHg) were consistent with the dimer mixture, 3,4-diethyl-2-hexenedinitrile and 1,3-dicyano-2-ethyl-3-hexene. The elemental analysis was also in agreement with this structure:

Calc. for $C_{10}H_{14}N_2$: C, 74.07%; H, 8.64%; N, 17.28%. Found: C, 75.40%; H, 8.83%; N, 17.27%.

IR=Infrared
NMR=Proton Nuclear Magnetic Resonance
GC=Gas Chromotography

EXAMPLE 2

In a 1000 cc rocking autoclave was placed 133.3 gm (1.64 moles) of 2-pentenenitrile, and 10 gm 5% ruthenium on alumina. The autoclave was sealed and 200 gm of liquid ammonia was added. The autoclave was then heated at 290° F. for 6 hours. On cooling, the reaction mixture was filtered from the supported metal. The crude mixture was then distilled under vacuum to give 30.4% of the colorless cyanoamine (Bpt=90° C. 15 mmHg) and and 13.4% of the colorless dimer (Bpt=98° C. at 1 mmHg) shown in Example 1.

EXAMPLE 3

In a 1000 cc rocking autoclave was placed 133.3 gm (1.64 moles) of 2-pentenenitrile and 10 gm of 5% ruthenium on alumina. The autoclave was sealed and 200 gm of liquid ammonia was added. The autoclave was then heated to 300° F. for 6 hours. On cooling, the reaction mixture was filtered from the supported metal. The crude mixture was then distilled under vacuum to give 32.2% of the colorless cyanoamine (Bpt=90° C. at 15 mmHg) and 12.3% of the colorless dimer (Bpt=98° C. at 1 mmHg) shown in Example 1.

EXAMPLE 4

In a 1000 cc rocking autoclave was placed 133.3 (1.64 moles) of 2-pentenenitrile, and 300 cc of aqueous ammonium hydroxide (28-30 weight %). The autoclave was sealed and heated to 305° F. for 6 hours. On cooling, the crude product was then distilled to give 68.2% cyanoamine 20.5% dicyanoamine. The component boiling at 90° C. at 15 mmHg was the cyanoamine shown in Example 1.

IR, NMR, and GC mass spectra of the component boiling at 117° C. at 3 mmHg were consistent with the dicyanoamine, N,N'-di-2-(1-cyanobutyl)amine.

IR=Infrared
NMR=Proton Nuclear Magnetic Resonance
GC=Gas Chromotography

EXAMPLE 5

In a 1000 cc rocking autoclave was placed 133.3 gm (1.64 moles) of 2-pentenenitrile, and 20 cc of water. The autoclave was sealed and 130 gm of liquid ammonia was added. The autoclave was then heated at 300° F. for 6 hours. On cooling, the reaction mixture was distilled under vacuum to give 64.0% of the cyanoamine and 11.9 combined % of the dimer of Example 1 and a dimer amine,

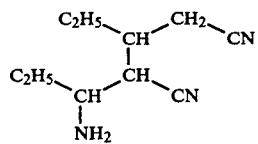

EXAMPLE 6

In a 500 cc rocking autoclave was placed 19 gm (0.12 mole) of dimer from Example 1, 50 cc methyl alcohol, and 15 gm of Raney nickel. The autoclave was sealed and 30 gm of liquid ammonia was added. The autoclave was then pressured to 2100 psi with hydrogen gas and heated to 215°-240° F. After 2 hours the hydrogen absorption was complete. On cooling, the reaction mixture was filtered from the catalyst and the methyl alcohol was removed by evaporation. The crude product was distilled under vacuum to give 41.8% of cyclized compounds and 35.4% of diamines. The IR, MNR, and GC mass spectra of the component boiling at 97° C. (15 mmHg) was consistent with cyclized products, 4,5-diethylhexamethyleneimine and 3-propyl-4-ethyl-piperidine. The elemental analysis was also in agreement with these structures:

Calc. for $C_5H_{18}N_2$: C, 78.43%; H, 12.41%; N, 9.15%. Found: C, 77.51%, H, 13.73%; N, 9.08%.

The IR, NMR, and GC mass spectra of the component boiling at 125° C. (0.3 mmHg) were consistent with amines, 3,4-diethyl-1,6-diaminohexane and 3-ethyl-4-aminomethyl-1-aminoheptane.

The elemental analysis was also in agreement with these structures:

Calc. for $C_{10}H_{22}N_2$: C, 70.58%; H, 12.94%; N, 16.47%. Found: C, 69.51%; H, 13.51%; N, 15.64%.

IR = Infrared
NMR = Proton Nuclear Magnetic Resonance
GC = Gas Chromotography

EXAMPLE 7

In a 500 cc rocking autoclave was placed 45.4 gm (0.46 moles) of the cyanoamine (from Example 2), 150 cc of methyl alcohol, and 25 gm of Raney nickel. The autoclave was sealed and 50 gm of liquid ammonia was added. The autoclave was then pressured to 2100 psi with hydrogen gas and heated to 215° F. After 1½ hours the hydrogen absorption was complete. On cooling, the reaction mixture was filtered from the catalyst and the methyl alcohol was removed by evaporation. The crude product was then distilled under vacuum (Bpt=64° C. at 15 mmHg) to give 76% yield of the colorless diamine, 1,3-diaminopentane. A potentiometric titration of the distilled product indicated that it was 98% diamine. IR, NMR, and GC mass spectra were consistent with the diamine as was the elemental analysis:

Calc. for $C_5H_{14}N_2$: C, 58.82%; H, 13.72%; N, 27.45%. Found: C, 57.00%; H, 13.60%; N, 26.21%.

EXAMPLE 8

To 100 parts of epoxy resin are based on diglycidyl ether of bisphenol A,

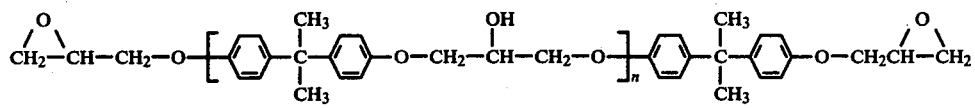

(n=0.2, WPE=185–195), 13.6 parts of 1,3-diaminopentane (Example 1) is added. After mixing thoroughly for 2 minutes and centrifuging for 3 minutes at the speed of 3000 rpm, this resin mixture is placed in the aluminum mold and cured for 2 hours at 80° C. and for another 2 hours at 150° C. in silicon oil bath.

The heat deflection temperature (ASTM D648-56) of the cured product shows 117.4° C. under the stress of 264 psi and heating rate of 2 degree/min.

IR = Infrared
NMR = Proton Nuclear Magnetic Resonance
GC = Gas Chromotography

The above Examples clearly indicate the preparation of the novel compounds of the present invention. Further, Example 8 illustrates the use of the polyamine derivatives of such novel compounds as epoxy curing agents.

Having thus described the invention, we claim:

1. A nitrogen containing compound represented structurally as

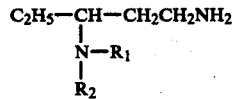

wherein $R_1$ is H and $R_2$ is $C_2H_5—CH—CH_2—CH_2NH_2$.

2. The compound of claim 1 wherein $R_1$ and $R_2$ are

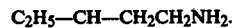

* * * * *